(12) United States Patent
Beguin et al.

(10) Patent No.: US 11,977,004 B2
(45) Date of Patent: May 7, 2024

(54) CAPILLARY-BASED PRESSURE THRESHOLD SENSOR FOR LIQUIDS AND METHODS AND APPARATUSES USING SAME

(71) Applicant: Becton, Dickinson and Company, Franklin Lakes, NJ (US)

(72) Inventors: Steve Beguin, Rathdrum (IE); John Adams, Dublin (IE); Danielle Aboud, Dublin (IE); Maurice Curtin, Blackrock (IE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 426 days.

(21) Appl. No.: 17/327,244

(22) Filed: May 21, 2021

(65) Prior Publication Data
US 2021/0381921 A1 Dec. 9, 2021

Related U.S. Application Data

(60) Provisional application No. 63/034,029, filed on Jun. 3, 2020.

(51) Int. Cl.
| | |
|---|---|
| *G01M 3/00* | (2006.01) |
| *A61M 5/168* | (2006.01) |
| *G01K 11/00* | (2006.01) |
| *G01M 3/16* | (2006.01) |

(52) U.S. Cl.
CPC .......... *G01M 3/16* (2013.01); *A61M 5/16854* (2013.01); *G01K 11/00* (2013.01); *A61M 2205/15* (2013.01); *A61M 2205/3331* (2013.01); *A61M 2205/3368* (2013.01)

(58) Field of Classification Search
CPC ................ G01M 3/16; A61M 5/16854; A61M 2205/15; A61M 2205/3331; A61M 2205/3368; G01K 11/00
USPC ............................................................ 73/40
See application file for complete search history.

(56) References Cited

U.S. PATENT DOCUMENTS

| | | |
|---|---|---|
| 6,491,061 B1 | 12/2002 | Lopez et al. |
| 6,843,272 B2 | 1/2005 | Schoeniger et al. |
| 8,101,431 B2 | 1/2012 | McDevitt et al. |
| 8,441,361 B2 | 5/2013 | McAlister |

(Continued)

OTHER PUBLICATIONS

A. Moghadama et al., Physicochemical and Engineering Aspects, "A New Approach to Modeling Liquid Intrusion in Hydrophobic Fibrous Membranes With Heterogeneous Wettabilities", Colloids and Surfaces A (2018), pp. 154-163.

(Continued)

*Primary Examiner* — Max H Noori
(74) *Attorney, Agent, or Firm* — Dickinson Wright PLLC

(57) ABSTRACT

Capillary-based pressure threshold sensors are provided for liquids that exploit the properties of hydrophobic, superhydrophobic, oleophobic and amphiphobic porous membranes to detect when fluid passes through the membrane in the event of the pressure across the membrane rising above the breakthrough pressure of a fluid. Example implementations are provided of different configurations for a capillary-based pressure threshold sensor, and of how a capillary-based pressure threshold sensor is used in a medication delivery device or other fluid delivery devices to detect occlusion or other fluid flow condition.

17 Claims, 12 Drawing Sheets

(56) References Cited

U.S. PATENT DOCUMENTS

| | | | |
|---|---|---|---|
| 8,545,248 B2 | 10/2013 | Davey et al. | |
| 2003/0062149 A1* | 4/2003 | Goodson | H01L 23/473 |
| | | | 257/E23.098 |
| 2005/0129867 A1* | 6/2005 | Picard | G11B 5/842 |
| | | | 427/180 |
| 2005/0138990 A1* | 6/2005 | Phillips | G01M 3/16 |
| | | | 73/40 |
| 2012/0183949 A1 | 7/2012 | Hyde et al. | |
| 2016/0166757 A1 | 6/2016 | Tatsuta | |
| 2020/0033336 A1* | 1/2020 | Kamei | B01L 3/5023 |
| 2022/0265462 A1* | 8/2022 | Alder | A61F 5/4404 |
| 2023/0062996 A1* | 3/2023 | Jackson | A61M 15/08 |
| 2023/0083056 A1* | 3/2023 | Acuna Cespedes | |
| | | | E21B 49/0875 |
| | | | 73/152.24 |
| 2023/0285899 A1* | 9/2023 | Schoenhaber | B01J 21/066 |
| | | | 60/297 |

OTHER PUBLICATIONS

Edward Bormashenko et al., "Why Do Pigeon Feathers Repel Water? Hydrophobicity of Pennae, Cassie-Baxter Wetting Hypothesis and Cassie-Wenzel Capillarity-Induced Wetting Transition", Journal of Colloid and Interface Science 311 (2007), pp. 212-216, www.sciencedirect.

David Y. Liang et al., "Systematic Characterization of Degas-Driven flow for Poly(Dimethylsiloxane) Microfluidic Devices", Biomicrofluidics 5, 024108 (2011), Published online Jun. 2, 2011, pp. 1-16.

Steve Beguin, "Multi-Electrode Array for High Resolution Impedance-Based Analysis of Adherent Cell Cultures", Swinburne University of Technology Faculty of Science, Engineering and Technology, Melbourne, Jun. 2019 ARC Training Centre in Biodevices, pp. 270.

Luigi Brancato, "Plasma Enhanced Hydrophobicity of Parylene-C Surfaces for a Blood Contacting Pressure Sensor", Eurosensors 2014, the XXVIII Edition of the Conference Series, Procedia Engineering 87 ( 2014 ) 336-339, ScienceDirect, www.sciencedirect.com.

Yanying Feng et al., "Passive Valves Based on Hydrophobic Microfluidics", Science Direct, Sensors and Actuators A 108 (2003), pp. 138-143, www.sciencedirect.com.

Hans-Dietrich Polaschegg et al., "A Fail-Safe Protective System Against Blood Loss to the Environment for Extracorporeal Circuits", @IEEE, Feb. 1992, 2 pages.

Francesco Dal Dosso et al., Supplementary Information "Innovative Hydrophobic Valve Allows Complex Liquid Manipulations in a Self-Powered Channel-Based Microfluidic Device", KU Leuven, Department of Biosystems—Biosensors Group, Belgium, 7 pages.

Francesco Dal Dosso et al., "Innovative Hydrophobic Valve Allows Complex Liquid Manipulations in a Self-Powered Channel-Based Microfluidic Device", @ 2019 American Chemical Society, ACS Sensors 2019, 4, pp. 694-703.

Mohammad Paknahad et al., "Diffusion-Based Humidity Control Membrane for Microfluidic-Based Gas Detectors", ScienceDirect , Analytica Chimica Acta 1021 (2018), pp. 103-112, www.elsevier.com/locate/aca.

Francesco Dal Dosso et al., "Self-Powered Infusion Microfluidic Pump for Ex Vivo Drug Delivery", Biomedical Microdevices (2018), Published online: May 31, 2018, 11 pages.

Neil J. Shirtcliffe et al., "An Introduction to Superhydrophobicity", Science Direct, Advances in Colloid and Interface Science 161 (2010), pp. 124-138, www.elsevier.com/locate/cis.

* cited by examiner

CAPILLARY-BASED PRESSURE THRESHOLD SENSOR FOR LIQUIDS AND METHODS AND APPARATUSES USING SAME This application claims the benefit of U.S. provisional application Ser. No. 63/034,029, filed Jun. 3, 2020, the contents of which is incorporated herein by reference in its entirety.

BACKGROUND

Field

The present disclosure relates generally to a sensing system that can detect an overpressure event in a fluid line or pathway. The present disclosure also relates to capillary-based pressure threshold sensors for liquids that exploit the properties of porous membranes to detect when fluid passes through the membrane in the event of the pressure across the membrane rising above the breakthrough pressure of the fluid.

Description of Related Art

Fluid delivery devices such as infusion pumps and infusion sets are known for delivering a medication or drug to a patient over a prolonged period time. Examples of infusion pumps include an ambulatory pump (e.g., a portable pump), a wearable pump or a patch pump, and a larger infusion pump for non-ambulatory care settings. An example infusion set includes a catheter assembly connected to a pump (e.g. MiniMed Paradigm® insulin pump by Medtronic) by a tubing set.

These fluid delivery devices typically include one or more fluid pathways such as tubing connected to the infusion set, or a fluid pathway within the infusion set that includes the catheter. An infusion pump can have internal fluid pathways that direct a fluid such as a medication from a reservoir to a catheter. Occlusions can occur in these fluid pathways. For example, an occlusion can be caused by mechanical problems with the infusion device, or by biologic or pharmacologic and/or mechanical obstruction caused by the fluid itself. It is important to determine a partial or total occlusion in drug delivery applications because failure to do so can cause the patient to not receive the prescribed drug therapy amount. One potential failure mode that can be caused by an occluded fluid path is a pressure increase that can cause a leak in the fluid path and subsequently missed dose(s). Increased pressure in the fluid delivery system can also cause other issues such as seizing of the pumping mechanism, slow down of the pumping mechanism and lengthening of overall delivery time, damage on the pumping mechanism caused by increased force needed to overcome increased pressure, stall of the pumping mechanism, and increased power consumption due to pumping mechanism operating at higher pressures.

A need therefore exists for an occlusion or pressure sensing element in a fluid pathway. Considerations for integrating a pressure sensing element in wearable or disposable medical devices are reliability, stability, size of the component and ability to be integrated in the device, price, power consumption, need for (re)calibration and computational power required. Existing pressure sensors can be too expensive to add to an infusion device while maintaining target cost of the device, and/or too unreliable to detect an overpressure condition, and/or require specialized sizeable hardware to read the value measured by the sensor value, and/or require excessive computing power to analyze the data provided by a pressure sensor.

SUMMARY

The above and other problems are overcome, and additional advantages are realized, by illustrative embodiments.

Example embodiments of the present disclosure provide a pressure detector that can be miniaturized to achieve a small footprint, uses materials that can be either sourced off the shelf or specially developed to meet particular requirements, achieves very low cost of goods, represents a failsafe element in a fluid path when configured to be the weakest point of the fluid delivery system, has low power consumption (e.g., zero power consumption in some embodiments), and requires low computational power (e.g., zero computational power in some embodiments), can be idle, and does not require calibration.

It is an aspect of illustrative embodiments to provide a method of making a capillary-based pressure threshold sensor comprising: selecting a first porous medium with a porous property that allows fluid to leak from a first side thereof, through the medium to an opposite second side thereof, the leak happening when fluid pressure exceeds the porous medium fluid breakthrough pressure threshold; and providing a fluid detection element disposed at least proximally to the second side of the porous medium and configured to detect the presence of at least the target fluid on said second side of the porous medium.

In accordance with aspects of illustrative embodiments, the fluid detection element is chosen from an passive fluid detection element and an active fluid detection element, wherein a passive fluid detection element is not activated until the target fluid leaks through the porous medium reaching the opposite second side of the porous medium, and an active fluid detection element provides different outputs that distinguish a first state wherein the target fluid has not yet leaked through the porous medium from a second state wherein the target fluid has leaked through the porous medium.

In accordance with aspects of illustrative embodiments, the fluid detection element comprises an indicator element that is configured to change state when the target fluid has leaked through the porous medium to the second side thereof, and changing state is chosen from a color indication and a change in color indication.

In accordance with aspects of illustrative embodiments, the method further comprises coating the first porous medium with a thermoresponsive material to detect a condition chosen from a designated temperature and a designated pressure change in the target fluid.

In accordance with aspects of illustrative embodiments, the thermoresponsive material is poly-N-isopropylacrylamide (PNIPAM).

In accordance with aspects of illustrative embodiments, the porous property of the medium is chosen from pore size, thickness, material, topography, coating, and contact angle with the fluid.

In accordance with aspects of illustrative embodiments, the method further comprises configuring the first side to form a seal over a port in a fluid pathway to expose the porous medium to fluid in the fluid pathway and prevent the fluid from leaking outside the capillary-based pressure threshold sensor.

In accordance with aspects of illustrative embodiments, the fluid detection element comprises at least two electrodes, and the method further comprises providing a second porous medium (-philic) disposed between the porous medium (-phobic) and the fluid detector element to controllably distribute the fluid leaking through the porous medium to the sensor, wherein the second porous medium is chosen to have different conductivity when dry and when wetted by the fluid in the fluid pathway; and providing the two electrodes in contact with the second side of the porous medium, the electrodes configured to be passive and not activated until fluid leaking through the porous medium exceeds the threshold.

In accordance with aspects of illustrative embodiments, providing a fluid detection element comprises providing electrodes made from contact pads on a printed circuit board (PCB).

In accordance with aspects of illustrative embodiments, the method further comprises heat-staking the PCB via heat-staking pins configured to maintain proximity with the second porous medium and direct contact with the porous medium.

In accordance with aspects of illustrative embodiments, the fluid detection element comprises at least two electrodes, and further comprising operating the electrodes as a passive switch that is open until it closes upon contact with the fluid.

In accordance with aspects of illustrative embodiments, providing a switch comprises providing electrodes made from contact pads on a printed circuit board (PCB).

In accordance with aspects of illustrative embodiments, the method further comprises connecting one of the electrodes to a ground pin of a microcontroller and connecting the other electrode to an input pin of the microcontroller.

In accordance with aspects of illustrative embodiments, the method further comprises connecting one of the electrodes to an output pin of a microcontroller and connecting the other electrode to an input pin of the microcontroller.

In accordance with aspects of illustrative embodiments, the method further comprises connecting one of the electrodes to a positive rail of a power supply or reference voltage having common ground with the microcontroller and connecting the other electrode to an input pin of the microcontroller.

In accordance with aspects of illustrative embodiments, the method further comprises connecting a pullup resistor between a positive rail of a power supply or reference voltage for the microcontroller and said input pin.

In accordance with aspects of illustrative embodiments, the method further comprises connecting a pulldown resistor between said input pin and a negative rail connected to the negative or ground terminal of the microcontroller.

In accordance with aspects of illustrative embodiments, wherein the resistor has a resistance on the order of 1 k Ohm to 100 M Ohm.

In accordance with aspects of illustrative embodiments, the porous medium is chosen from a hydrophobic medium, a superhydrophobic medium, an oleophobic medium, and an amphiphobic porous medium.

In accordance with aspects of illustrative embodiments, the method further comprises selecting a second porous medium disposed at least proximally to the first side of the first porous medium as to be in contact with the target fluid at least before target fluid leak through the first porous medium, wherein second porous medium has a porous property that: allows fluid to readily infiltrate said second porous medium; and a has porous property that will prevent gas to pass through the second porous medium after it is infiltrated with said target fluid until gas exceeds said second porous medium gas entry pressure.

In accordance with aspects of illustrative embodiments, the method further comprises selecting a supplementary porous medium disposed at least proximally to the opposite side of the first porous medium as to be in contact with the target fluid at least before target fluid leak through the first porous medium, wherein second porous medium has one or more porous properties that allows fluid to readily infiltrate the second porous medium and achieves enhanced contact between the target fluid and the fluid detection element.

It is an aspect of illustrative embodiments to provide a method of using a capillary-based pressure threshold sensor comprising: selecting an overpressure threshold to be detected within a fluid; selecting a capillary-based pressure threshold sensor comprising porous medium having at least one porous property and a fluid breakthrough pressure threshold related to the overpressure threshold, the capillary-based pressure threshold sensor allowing fluid to leak from one side thereof, through the medium to an opposite side thereof when fluid pressure across the medium exceeds the fluid breakthrough pressure threshold; and placing the capillary-based pressure threshold sensor such that at least one side of the porous medium comes in contact with fluid for which an overpressure event is to be detected.

In accordance with aspects of illustrative embodiments, the method further comprises providing a fluid pathway and selecting the location where the overpressure event shall be detected by the capillary-based pressure threshold sensor.

In accordance with aspects of illustrative embodiments, the method further comprises providing a fluid reservoir and selecting the location where the overpressure event shall be detected by the capillary-based pressure threshold sensor.

In accordance with aspects of illustrative embodiments, the method further comprises providing a port at the selected location and securing the porous medium over the port to seal the port.

In accordance with aspects of illustrative embodiments, the method further comprises welding the porous medium onto material forming the fluid pathway.

In accordance with aspects of illustrative embodiments, wherein the capillary-based pressure threshold sensor comprises at least two electrodes, further comprising operating the electrodes as a passive switch that is open until it closes upon contact with the fluid.

In accordance with aspects of illustrative embodiments, the method further comprises triggering a notification when the passive switch is closed.

In accordance with aspects of illustrative embodiments, triggering is chosen from providing an input associated with the notification to a microcontroller connected to the electrodes, and generating an indication by inducing a change in an indicator element in response to the fluid contacting at least one side of the porous medium.

In accordance with aspects of illustrative embodiments, the method further comprises connecting one of the electrodes to a ground pin of the microcontroller and connecting the other electrode to an input pin of the microcontroller.

In accordance with aspects of illustrative embodiments, the method further comprises connecting one of the electrodes to an output pin of a microcontroller and connecting the other electrode to an input pin of the microcontroller.

In accordance with aspects of illustrative embodiments, the method further comprises connecting one of the electrodes to a positive rail of a power supply having common ground with the microcontroller and connecting the other electrode to an input pin of the microcontroller.

In accordance with aspects of illustrative embodiments, the method further comprises connecting a pullup resistor to a positive rail of a power supply or reference voltage for the microcontroller and an input pin.

In accordance with aspects of illustrative embodiments, the method further comprises connecting a pulldown resistor between an input pin and a negative rail connected to the negative or ground terminal of the microcontroller.

In accordance with aspects of illustrative embodiments, the resistor has a resistance on the order of 1 k Ohm to 100 M Ohm.

In accordance with aspects of illustrative embodiments, wherein the porous medium is chosen from a hydrophobic medium, a superhydrophobic medium, an oleophobic medium, and an amphiphobic porous medium.

In accordance with aspects of illustrative embodiments, the at least one porous property of the medium is chosen from pore size, thickness, material, topography, coating, and contact angle with the fluid.

It is an aspect of illustrative embodiments to provide a capillary-based pressure threshold sensor comprising a porous medium having at least one porous property and a fluid breakthrough pressure threshold that allows fluid to leak from a first side thereof, through the medium to an opposite second side thereof when fluid pressure exceeds a porous medium fluid breakthrough threshold; and a fluid detection element disposed at least proximally to the second side of the porous medium and configured to detect the presence of at least the target fluid on the second side of the porous medium.

In accordance with aspects of illustrative embodiments, the capillary-based pressure threshold sensor further comprises two electrodes in contact with the second side of the porous medium.

In accordance with aspects of illustrative embodiments, the porous medium is chosen from a hydrophobic medium, a superhydrophobic medium, an oleophobic medium, and an amphiphobic porous medium.

In accordance with aspects of illustrative embodiments, the at least one porous property of the porous medium is chosen from pore size, thickness, material, topography, coating, and contact angle with the fluid.

In accordance with aspects of illustrative embodiments, the porous medium is a first porous medium and further comprising a second porous medium disposed at least proximally to the first side of the first porous medium as to be in contact with the target fluid at least before target fluid leak through the first porous medium, wherein second porous medium has one or more porous properties allow fluid to readily infiltrate said second porous medium and prevent gas to pass through the second porous medium after it is infiltrated with the target fluid until gas exceeds the second porous medium gas entry pressure.

In accordance with aspects of illustrative embodiments, the capillary-based pressure threshold sensor further comprises a supplementary porous medium disposed at least proximally to the opposite side of the first porous medium as to be in contact with the target fluid at least before target fluid leak through the first porous medium, wherein second porous medium has one or more porous properties that allows fluid to readily infiltrate said second porous medium and enhances contact between the target fluid and the fluid detection element.

In accordance with aspects of illustrative embodiments, the supplementary porous medium is chosen from a hydrophilic medium, a superhydrophilic medium, an oleophilic medium, and an amphiphilic porous medium.

In accordance with aspects of illustrative embodiments, the supplementary porous medium is chosen from a material that swells when contacted by the fluid in the fluid pathway, and the fluid detection element operates as a passive switch that is activated by swelling of the second porous medium.

In accordance with aspects of illustrative embodiments, the fluid detection element comprises two electrodes in contact with the supplementary porous medium.

In accordance with aspects of illustrative embodiments, the supplementary porous medium is chosen to have different conductivity when dry and when wetted by the fluid in the fluid pathway.

In accordance with aspects of illustrative embodiments, the fluid detection element comprises two electrodes made from contact pads on a printed circuit board (PCB).

In accordance with aspects of illustrative embodiments, the PCB is heat-staked via heat-staking pins to maintain proximity with the second porous medium and direct contact with the porous medium.

In accordance with aspects of illustrative embodiments, the fluid detection element comprises at least two electrodes operable as a passive switch that is open until it closes upon contact with the fluid.

In accordance with aspects of illustrative embodiments, the capillary-based pressure threshold sensor further comprises an indicator element configured to change state when the target fluid has leaked through the porous medium to the second side thereof, and changing state is chosen from a color indication and a change in color indication.

In accordance with aspects of illustrative embodiments, the fluid detection element, when closed, triggers a notification that can be processed by a microcontroller connected to the electrodes.

In accordance with aspects of illustrative embodiments, one of the electrodes is connected to a ground pin of the microcontroller and the other electrode is connected to an input pin of the microcontroller.

In accordance with aspects of illustrative embodiments, one of the electrodes is connected to an output pin of a microcontroller and the other electrode is connected to an input pin of the microcontroller.

In accordance with aspects of illustrative embodiments, one of the electrodes is connected to a positive rail of a power supply having common ground with the microcontroller and the other electrode is connected to an input pin of the microcontroller.

In accordance with aspects of illustrative embodiments, the capillary-based pressure threshold sensor further comprises a pulldown resistor connected between said input pin and a negative rail connected to the negative or ground terminal of the microcontroller.

In accordance with aspects of illustrative embodiments, the capillary-based pressure threshold sensor further comprises a pullup resistor connected to a positive rail of the power supply or reference voltage for the microcontroller and the input pin.

In accordance with aspects of illustrative embodiments, the pullup resistor has a resistance on the order of 1 k Ohm to 100 M Ohm.

In accordance with aspects of illustrative embodiments, the fluid detection element is passive and not activated until the target fluid leaks through the porous medium reaching the opposite second side of the porous medium.

In accordance with aspects of illustrative embodiments, the fluid detection element is active and provides different outputs that distinguish a first state wherein the target fluid has not yet leaked through the porous medium from a second state wherein the target fluid has leaked through the porous medium.

In accordance with aspects of illustrative embodiments, the capillary-based pressure threshold sensor further comprises a thermoresponsive material coating the first porous medium to detect a condition chosen from a designated temperature and a designated pressure change in the target fluid.

In accordance with aspects of illustrative embodiments, the thermoresponsive material is poly-N-isopropylacrylamide (PNIPAM).

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims

BRIEF DESCRIPTION OF THE DRAWINGS

The above and/or other aspects and advantages of embodiments of the illustrative embodiments will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1A:
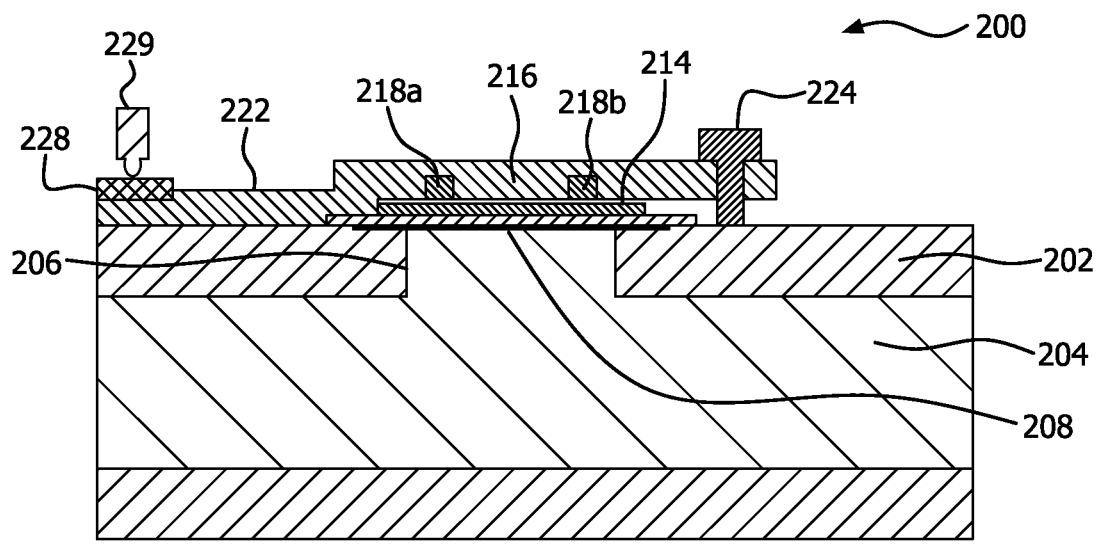
FIG. 1A depicts a side view diagram of a capillary-based pressure threshold sensor constructed in accordance with an illustrative embodiment.

Reference will now be made in detail to illustrative embodiments, which are depicted in the accompanying drawings. The embodiments described herein exemplify, but do not limit, the illustrative embodiments by referring to the drawings.

Figure 1B:
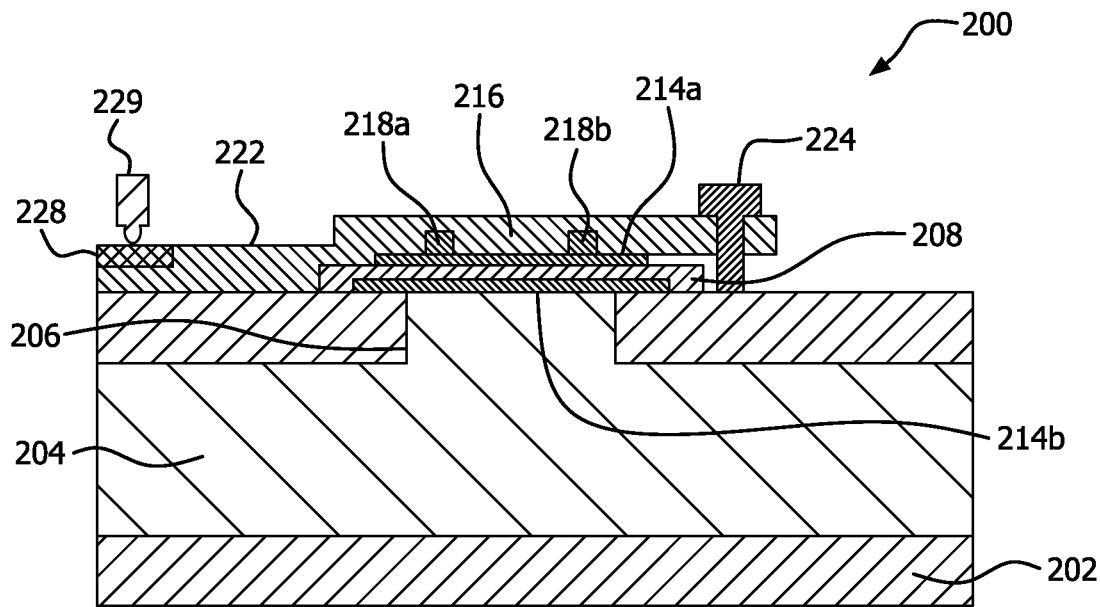
FIG. 1B depicts a side view diagram of a capillary-based pressure threshold sensor with a hydrophilic porous medium in contact with the fluid path that, once wet/primed, prevents air from being introduced in the fluid path as a result of negative pressure in the fluid path in accordance with an illustrative embodiment.

In accordance with the present disclosure, a capillary-based pressure threshold sensor 200 is presented that uses hydrophobic porous material or medium 208 and that medium's intrinsic property of fluid breakthrough pressure (e.g., a capillary-based pressure threshold) to detect a desired overpressure condition or event in a given application such as detecting overpressure in a fluid pathway in a fluid delivery application. FIGS. 1A and 1B each illustrate an example capillary-based pressure threshold sensor 200 implemented on a fluid pathway 202 formed by a material such as a polymer material to enclose a fluid 204. As described in more detail below, the sensor 200 on the fluid pathway 202 is used to detect when its membrane 208, and an optional membrane 214, is compromised after fluid pressure in the fluid pathway exceeds a designated threshold as an indicator for occlusion, for example, or other condition.

Figure 2A:
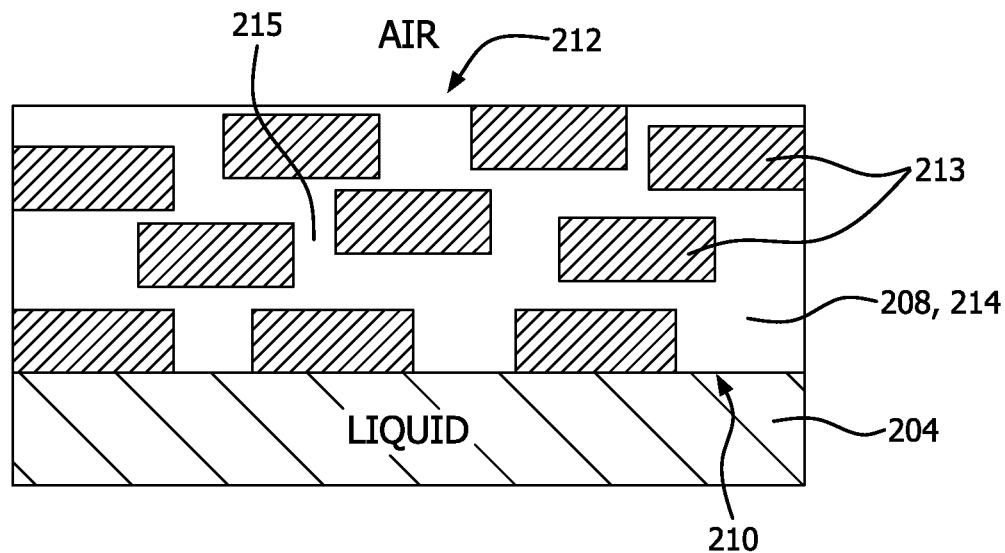
FIG. 2A depicts an example -phobic porous medium in the capillary-based pressure threshold sensor shown in FIG. 1A.

FIG. 2A illustrates a partial view of an example medium 208, 214 used in the sensor 200 that has a first side 210 in contact with a liquid 204, and a second side 212 in contact with a gas such as air. The capillary-based pressure threshold sensor 200 for liquids exploits the properties of a -phobic porous medium (e.g., hydrophobic, superhydrophobic, oleophobic and amphiphobic porous membranes) as the membrane 208, and optionally the properties of a -philic porous medium (e.g., hydrophilic, superhydrophilic, oleophilic and amphiphilic porous membranes) as the membrane 214, to detect when fluid 204 passes through the membrane 208 or 214 in the event of the pressure across the membrane 208 or 214 rising above the breakthrough pressure of the fluid 204. Capillary pressure p is a function of contact angle θ, surface tension γ, effective radius r of the interface with respect to the following equation:

$$p = \frac{2\gamma \cos\theta}{r}$$

Figure 2B:
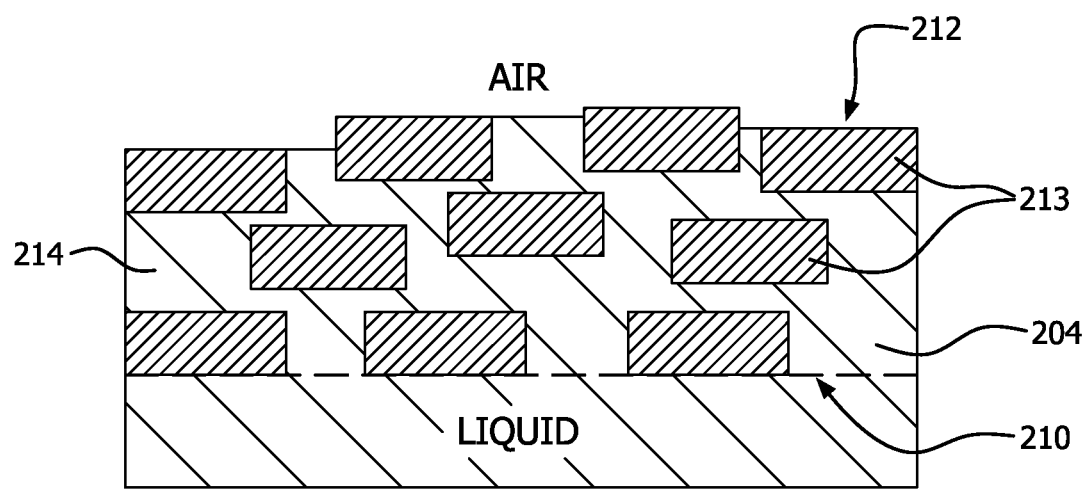
FIG. 2B depicts an example -philic porous medium in the capillary-based pressure threshold sensor shown in FIG. 1B that is wet by liquid, which will prevent air to enter the medium due to capillary forces.

For a porous membrane, the fluid breakthrough pressure is dictated by the capillary pressure of the equivalent largest pore 215 defined by corresponding adjacent fibers 213 in the membrane, as shown in FIG. 2A. The equivalent largest pore is the smallest pore the liquid has to pass through in a given percolated path among the fibers 213, going from one side 210 of the membrane to the other side 212. In addition to the hydrophilic porous membrane and/or swelling material 214a, FIG. 2B shows a -philic porous medium for membrane 214b that, when wetted by liquid 204, which will prevent air from entering the medium 214 due to capillary forces. It is to be understood that the capillary pressure can be positive (e.g., -philic porous medium) or negative (-phobic porous medium). Negative capillary pressures will prevent the passage of liquid but will allow the passage of gas, whereas positive capillary pressures will allow easy passage of liquid but will prevent passage of gas once wetted by said liquid.

Figure 3B:
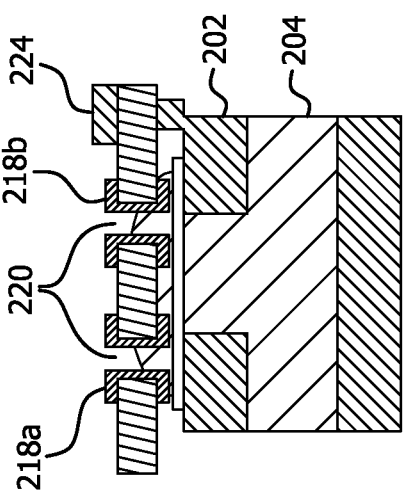
FIGS. 3A and 3B depict the capillary-based pressure threshold sensor in two different states, under the pressure threshold and above the pressure threshold respectively, constructed in accordance with an illustrative embodiment.
Figure 3A:
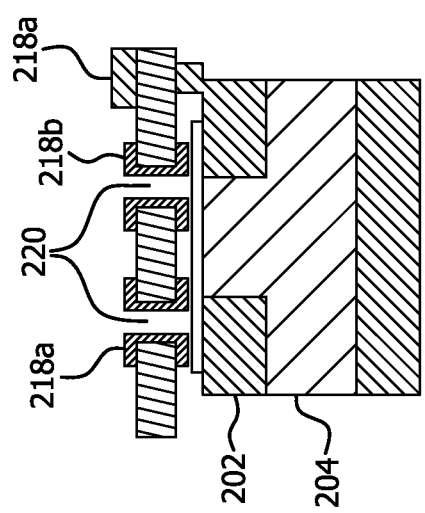

With reference to FIGS. 1A, 3A and 3B and in accordance with example embodiments, the capillary-based pressure threshold sensor 200 is formed by using a hydrophobic, superhydrophobic, oleophobic or amphiphobic porous medium (i.e., also referred to as "-phobic porous medium") for the hydrophobic membrane 208 in contact with the fluid 204 of a fluid line or pathway 202. For example, FIG. 3A illustrates sensor 200 operation when sensed fluid is under the fluid breakthrough pressure threshold, and FIG. 3B illustrates sensor 200 operation when sensed fluid is above the fluid breakthrough pressure threshold. In one example embodiment, the hydrophobic membrane 208 is a superhydrophobic porous membrane that seals a port 206 formed along a fluid pathway 202. The sensor 200 comprises a fluid detector or fluid detection element 216 (e.g., a passive switch or an active switch comprising electrodes 218a,b) for detecting the presence of a target fluid 204 that is placed in proximity, or in direct contact, with the porous membrane 208 to detect the presence of the fluid 204 after the fluid has crossed the membrane 208. For example, switch 216 can be a gold fingers or membrane switch. The properties of the porous medium used as the membrane 208 (e.g., pore size, thickness, material, topography, coating, and contact angle with the fluid, among others) are selected to obtain the desired fluid breakthrough pressure, where the fluid breakthrough pressure is the pressure at which the capillary pressure preventing the filling of the pores by the fluid is overcome by the pressure difference between the two sides 210, 212 of the porous membrane 208.

With continued reference to FIGS. 1B, 3A and 3B, a second porous membrane 214 (i.e., also referred to as "-philic porous medium") can be optionally intercalated between the fluid detector 216 and the -phobic porous medium 208 to allow the fluid 204 to spread in a controlled manner and optimize its detection by the fluid detector 216. In one embodiment, the -philic porous medium 214 expands to further improve contact with the fluid detector 216 once in contact with fluid to optimize detection. In another embodiment, the expanding -philic porous medium 214 triggers an example fluid detector element 216 (e.g., a switch) by mechanical action. In an example embodiment, the -phobic porous medium 208 is welded on the polymer material forming the fluid pathway 202 in such a way to seal a port 206 formed by a hole in the polymer material giving access to the fluid line or pathway 202. In an example embodiment, the fluid detector 216 is formed by two electrodes 218a,b in direct contact with the -philic porous medium 214. The -philic porous medium 214 is selected to have electrical conductivity different when dry than when wetted with the fluid 204. The presence of fluid can then be detected by means of a change of resistance between the two measuring electrodes 218a,b. If the fluid 204 has low electrical conductivity, (e.g. pure water), an ionic compound (such as salts) may be placed in the path between the fluid line 202 and the electrodes 218a,b of the fluid detector 216 to increase the conductivity of the fluid 204 and allow for its detection. Pogopins 229 and adjacent contact pads 228 in FIGS. 1A and 1B can be used to connect the circuit (i.e., the electrodes 218a,b) to a separate PCB that has a microcontroller or other components.

As shown in FIGS. 3A and 3B, venting-type electrodes 218a,b can be used. For example, vias 220 at the locations of sensing electrodes 218a,b allow air to escape and effectively direct the fluid 204 to contact the electrodes. Venting-type electrodes 218a,b are advantageous because they avoid pockets of air or bubbles trapped at the electrode that could prevent suitable electrical contact location and therefore impair the detection of the fluid 204.

Figure 4:
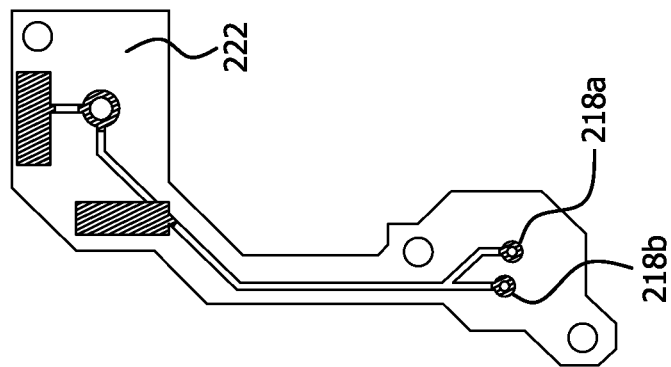
FIG. 4 depicts a printed circuit board comprising electrodes for a capillary-based pressure threshold sensor constructed in accordance with an illustrative embodiment.
Figure 5A:
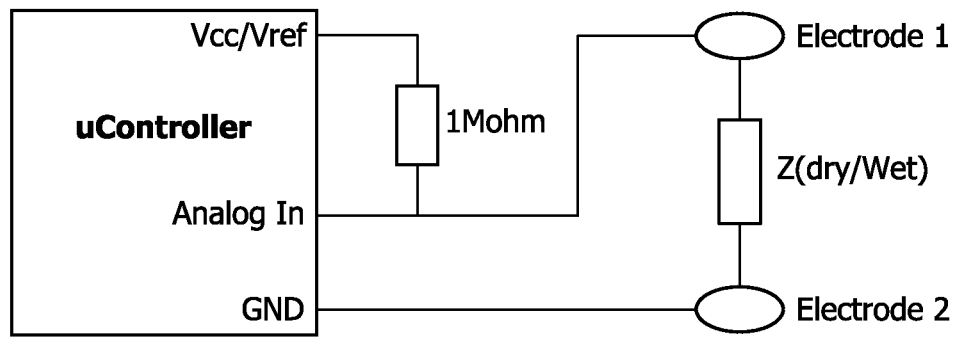
FIG. 5A is a block diagram of a capillary-based pressure threshold sensor constructed in accordance with an illustrative embodiment providing an output to a processor.
Figure 5B:
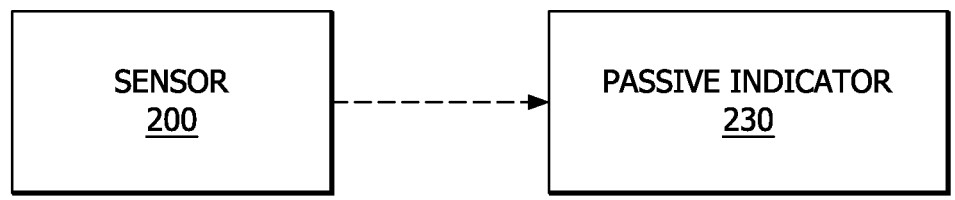
FIG. 5B is a block diagram of a capillary-based pressure threshold sensor providing an output to a passive indicator in accordance with an illustrative embodiment.

With reference to FIGS. 3A, 3B and 4, in an example embodiment, the electrodes 218a,b are made from contact pads on a printed circuit board (PCB) 222. The PCB 222 is heat-staked by means of heat-staking pins 22 to maintain close contact with the -philic porous medium 214, and the -philic porous medium 214 is in direct contact with -phobic porous medium 208. The electrodes 218a,b of the fluid detector 216 can act as an open switch that which closes upon contact with the fluid 204 to trigger a notification that can be processed by a microcontroller 226 or other type of processing device, as illustrated in FIG. 5A, or a passive indicator 230 can be used to generate a passive notification as illustrated in FIG. 5B. One electrode 218a may be connected to a ground pin of the microcontroller 226, and the other electrode 218b may be connected to an input pin of the microcontroller 226. A pullup resistor 232 with high value (e.g. 100 kOhm) can be connected to the positive rail of a power supply (not shown). The pullup resistance can be in the range of 1 k Ohm to 100 M Ohm, with a value relative to the impedance of the wet/dry electrodes indicated generally 234 in FIG. 5A. Pullup and pulldown resistors can be used interchangeably by connecting the electrodes 218a,b and pins of the microcontroller 226 appropriately. Such an embodiment has the advantage of having extremely low power consumption from the sensor 200 as long as no overpressure condition or event occurs in the fluid line 202 in which the sensor 200 is placed. In another example embodiment, the fluid 204 lowers the conductivity sensed by the electrodes 218a,b and triggers an event detectable in a similar way as previously described. In an example embodiment, one of the electrodes can be connected to an output pin of a microcontroller and the other electrode connected to an input pin of the microcontroller. In another example embodiment, one of the electrodes is connected to a positive rail of a power supply having common ground with the microcontroller and the other electrode is connected to an input pin of the microcontroller. In another embodiment, the electrodes are supplied with an alternating signal instead with or without DC bias.

It is to be understood that the description of the fluid detector 216 herein is as a functional switch for example purposes and not necessarily as an electric component. For example, the resistance of the fluid detector 216 operating as a "closed switch" is relatively high (e.g., several kiloOhms depending on the geometry of the electrodes 218 such as their material, properties of fluid, and so on), as opposed to a typically electric switch component wherein the resistance of the closed switch in typically on the order less than 1 Ohm. In accordance with example embodiments herein, the electrodes 218 are being used as a capacitive sensor.

Further, in accordance an example embodiment, the fluid detection element 216 is passive and not activated until the target fluid leaks through the porous medium reaching the opposite second side of the porous medium. In accordance with an alternative embodiment, the fluid detection element 216 is active and provides different outputs or readings (e.g., for a processor) that distinguish a first state wherein the target fluid 202 has not yet leaked through the porous medium 208 from a second state wherein the target fluid 202 has leaked through the porous medium 208. In an example embodiment, the presence of fluid can be detected by means of optical, capacitive, inductive or humidity sensors 216. In an embodiment illustrated in FIG. 5B, the fluid detector 216 operates directly with an indicator (e.g., the presence of fluid 202 induces a color change in a material associated with the fluid detector 216 that acts as fully passive indicator) without using a processor as illustrated in FIG. 5A. The passive indicator can operate as an optical or visual indicator that visually indicates (e.g., to the unaided eye of a user) a change in state such as a color change from when the fluid detector 216 is not in contact with the fluid 200 to when the fluid leaks through or otherwise comes into contact with the membrane(s) 208 and the fluid detector 216. Such an implementation can be useful, for example, in smartphones or other device with IPX8 specifications wherein, if a fluid detector 216 disposed in the housing or case of a smartphone or other case IPX8-rated device is subjected to fluid pressures higher than the IPX8 specification, then a passive indicator associated with the fluid detector 216 would be triggered, thereby voiding the warranty.

Although FIG. 4 illustrates a PCB 222 providing with traces between electrodes 218a,b and vias for wired connection to pins of a processing device 226, the sensor 200 can be provided with a wireless communication capability to communicate, at a minimum, a fluid detector 216 state change to a processing device 226. For example, there are some techniques used currently to power wireless sensors such as providing wireless power inductively, through radio frequency energy transfer, or capacitively as described in U.S. Patent Application Publication No. 2008/0129475. In this patent publication, RFID or SAW are recommended for sensor powering. One of these techniques can be used to provide enough power and signal amplification to allow the wireless transfer of information (e.g., a notification from the fluid detector 216 that fluid is sensed and therefore the switch 216 is activated) from the sensor 200 to the interrogator in the device (e.g., a drug delivery device) in which sensor 200 is deployed or another device (e.g., a user interface). Alternatively, the fluid detector 216 can be configured to passively In another example embodiment, the -philic porous medium 214 in FIG. 1A and 214a in FIG. 1B is a swelling -philic material that mechanically triggers a switch when it swells (e.g., as the result of fluid 204 leaking therethrough). The -philic porous medium 214 can be a porous material that expands or swells when absorbing liquid 204 such as a hydrophilic membrane and/or swelling membrane 214, thereby forcing close contact of the -philic porous medium 214 against the electrodes 218a,b. The swelling -philic material can be a dehydrated hydrogel, a foam or a sponge-like material, for example. The dehydrated hydrogel can be further loaded with salts or materials increasing the conductivity of the liquid-loaded material to improve the reliability of the detection of the fluid via the electrodes.

In accordance with another example embodiment, the capillary-based pressure threshold sensor 200 is a single use sensor (e.g., no longer useful once it leaks fluid 204 into the membrane and the fluid detector 216 is activated). In another embodiment, the capillary-based pressure threshold sensor 200 can be re-used after the fluid 204 that has passed through the -phobic porous medium 208 has evacuated the area probed by the fluid detector 216.

In accordance with another example embodiment, a -phobic porous medium (not shown) with higher fluid breakthrough pressure than that -phobic porous medium 208 is placed atop the sensor 200 to encapsulate the sensing area and prevent any fluid 204 from leaking beyond the detecting area and also provide a barrier to avoid water condensation that could generate a false positive detection. In accordance with another example embodiment, the contact between the electrodes 218a,b and the -philic porous medium 214 can be improved by having a roughened surface on the electrodes 218a,b, and/or having conducting material crimping the -philic porous medium 216, and/or having conducting material infiltrated in the -philic porous material 214 such as conducting glue that connects the porous material 214 and the individual electrodes 218a,b without short-circuiting the electrodes, and/or by having interdigitated electrodes. In accordance with another example embodiment, the sensor 200 can have more than the two electrodes 218a,b and a multiple sensor configuration. Different electrodes, for example, can be configured and functionalized to detect various fluid properties, including advanced fluid properties that can be further analyzed by electrochemical measurements and/or impedance spectroscopy. As a further example, thermosensitive material for the hydrophobic membrane (e.g., poly-N-isopropylacrylamide or PNIPAM) can be used. In one example embodiment, a material with contact angle varying with specific condition may be selected to combine the detection of multiple factors in addition to the fluid line overpressure. For example, a porous medium 208 constituted of or coated with a thermoresponsive material such as PNIPAM to detect either a temperature below the lower critical solution temperature (LCST) or a pressure above the fluid breakthrough pressure.

Figure 6:
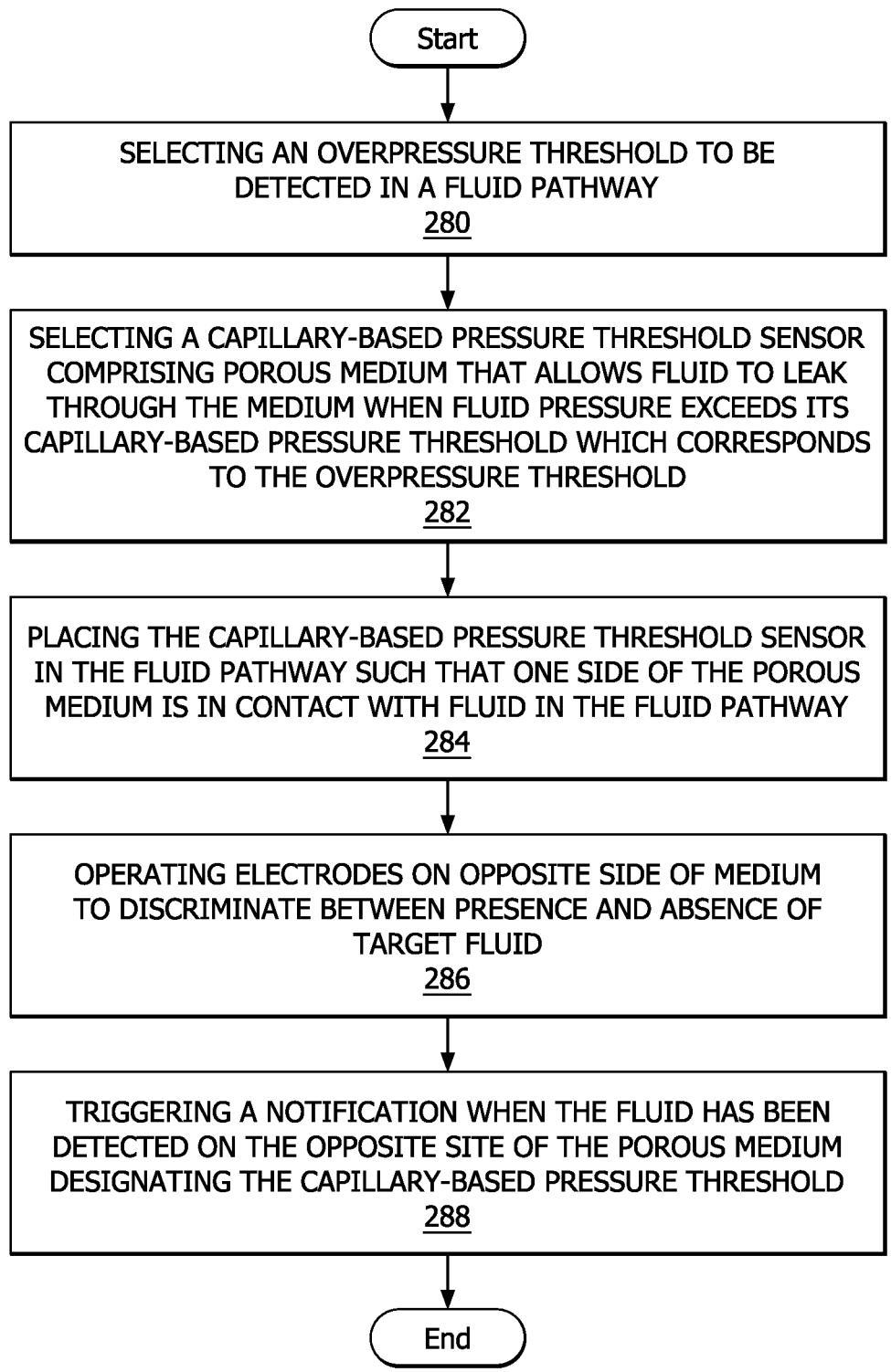
FIG. 6 is a flow chart illustrating an example method of using a capillary-based pressure threshold sensor constructed in accordance with an illustrative embodiment.

In accordance with the example embodiments, a method of making and using the capillary-based pressure threshold sensor 200 is illustrated in FIG. 6. For example, for a given application such as a desire to detect an overpressure condition is a fluid line (e.g., a fluid pathway between a reservoir with insulin and a catheter in a drug delivery device), an overpressure threshold to be detected in a fluid pathway 202 is selected (block 280). A capillary-based pressure threshold sensor is selected that comprises a porous medium 208 which allows fluid to leak through the medium when fluid pressure exceeds its fluid breakthrough pressure threshold (block 282). The porous medium 208 has at least one porous property and a fluid breakthrough pressure threshold related to the overpressure threshold. The capillary-based pressure threshold sensor 200 is placed along the fluid line or pathway 202 such that one side 210 of the porous medium 208 is in contact with fluid 204 in the fluid pathway 202 (block 284). The sensor 200 has electrodes 218a,b on the opposite side 212 of medium 208 which can operate as a switch that is open until it is closed upon contact with the fluid 204 (block 286). The closure of the switch 216 triggers a notification (e.g., an optical or color change indication from a passive type of switch 216, or an output from an active type of switch 216 to a processing device 226) (block 288). It is to be understood that the capillary-based pressure threshold sensor 200 is useful for detecting pressure in different types of fluid lines 202, with respect to different types of fluids, and in different types of fluid devices or systems, and therefore is not limited to drug delivery devices and fluid medicaments.

Some example materials for making a capillary-based pressure threshold sensor 200 with now be described. For an example, superhydrophobic porous membranes (e.g., Millipore SureVent® PVDF Membrane) can be used as the medium 208. The fluid detector 216 can be made, for example, of conductive traces contacted by the liquid (e.g., applicable to Pegfilgrastim and insulin), conductive pads or membrane switch present on a rigid or flexible PCB 222. Conductive pads can be made of, but are not limited to, gold/copper/tinned/Ag/AgCl material. Table 1 below provides example porous membrane properties and corresponding fluid breakthrough pressure for water (psi) for one type of SureVent PVDF superhydrophobic material. It is to be understood that the relationship between pore size, thickness, and fluid breakthrough pressure can vary from Table 1. For example, water breakthrough pressure can be different for a different material or coating (i.e., resulting in different contact angle) having the same pore size and thickness properties in Table 1.

TABLE 1

| Pore size (μm) | 0.1 | 0.22 | 0.45 | 0.65 | 1 | 2-5 |
|---|---|---|---|---|---|---|
| Thickness (μm) | 80-140 | 100-150 | 90-140 | 90-140 | 90-140 | 90-175 |
| Water breakthrough pressure (psi) | 73 | 45 | 25 | 15 | 7 | 2 |

A capillary-based pressure threshold sensor 200 constructed in accordance with example embodiments can be implemented in flexible or rigid fluid pathway 202. The configuration with a hydrophobic porous membrane 208 (e.g., with an optional hydrophilic material 214, the fluid detection system or element 216 (e.g., electrodes 218a,b, or mechanical or optical or other type of switch) can potentially be integrated anywhere on the fluid path so long as the -phobic porous membrane 208 is in contact with the fluid 204 in the fluid line 202 where overpressure detection is required or sought.

Underlying technical principles of the example embodiments of the capillary-based pressure threshold sensor 200 are capillary pressure of -phobic porous media 208 (e.g., hydrophobic medium), and conductivity of a porous medium 208, 214 when wetted with liquid solutions. In accordance with one example embodiment, the fluid 204 is conductive and crosses the -phobic porous membrane 208, and detection of an overpressure event is by closing an open circuit 216 via a change in the resistance of an optional second medium 214 (e.g., a sponge material). If no optional second medium 214 is used in the sensor 200, then fluid 204 itself replaces air in a gap between the electrodes 218a,b and closes a circuit between the electrodes. In accordance with another example embodiment, one of the electrodes 218a,b is excited (e.g., using capacitance versus a DC circuit) and measurements are made. Either way, a change in impedance of the medium in the area of the electrodes 218a,b by medium saturation of fluid can be measured to determine an overpressure event.

As stated above, a number of factors can be considered when selecting a -phobic porous material for the medium 208 that has porous properties and corresponding breakthrough pressure to achieve a desired pressure threshold for an application wherein an overpressure event is sought to be detected. For example, the medium 208 can employ a superhydrophobic porous membrane. Different properties of -phobic porous materials (e.g., roughness, pore size, material, coating, thickness of membrane, and so on) can impact the decision on which one has the breakthrough pressure that corresponds to the desired pressure threshold that is sought to be detected when exceeded.

Figure 8:
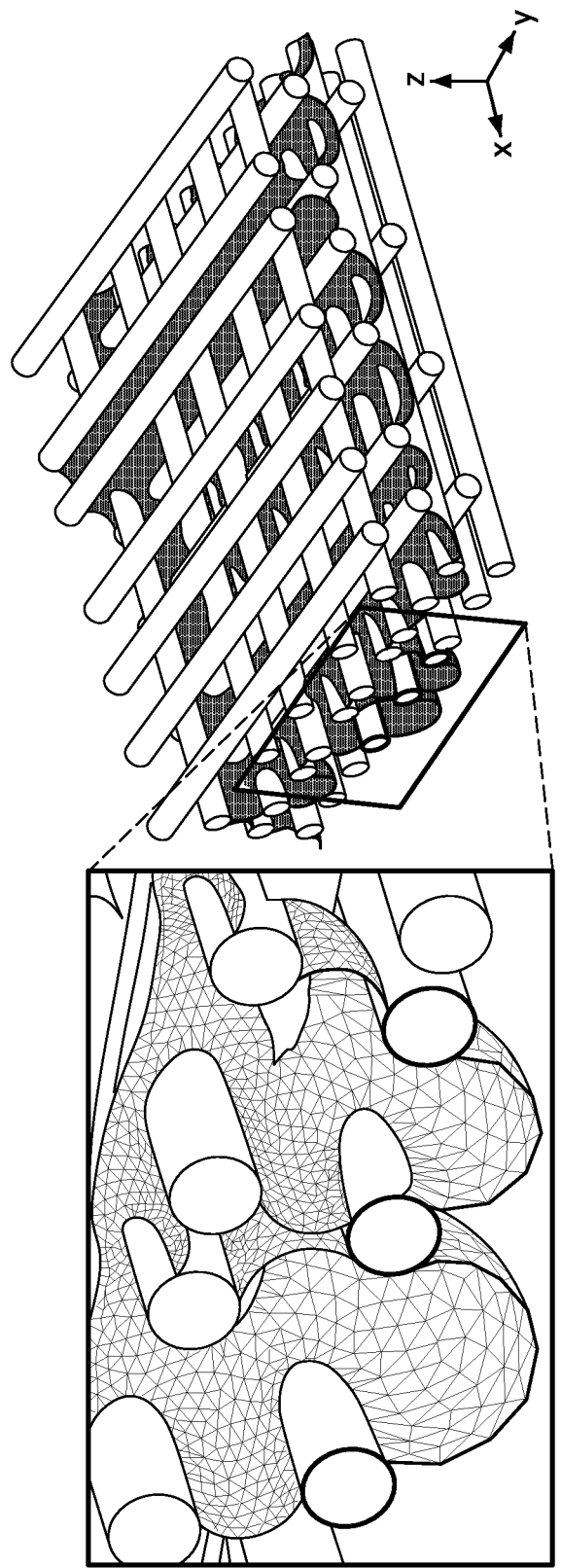
FIG. 8 is a representation of an air water intrusion of an example hydrophobic fibrous membrane.

Capillarity is the major factor in characterizing the nature of fluid interaction with a porous material. Fibrous materials with negative capillary pressure are hydrophobic and they can be used as a membrane or as a water-resisting barrier for a variety of applications. Precise capillary pressure prediction is also important for proper design of gas diffusion layers (GDLs) for fuel cells or other applications involving fluid-fluid or fluid-gas separation. FIG. 8 shows a magnified view of an air water interface undergoing the burst instability near the bottom of the membrane. Surfaces with hydrophobic tendencies can be enhanced to superhydrophobicity by the addition of roughness or, more accurately, a certain type of topography as illustrated by the example fibrous membrane in FIG. 8. When a hydrophobic fibrous membrane (e.g., a distillation membrane used in direct contact membrane distillation) is brought into contact with water, the hydrophobic fibers resist against water intrusion into the pores of the membrane (space between the fibers). Nevertheless, a submerged hydrophobic membrane cannot remain dry under elevated pressures. This is because the interface between the water outside the membrane and the air inside the membrane becomes unstable under excessive pressures, leading to water entering the pores of the membrane (i.e., the membrane's capillary pressure fails to balance the intrusion pressure). The pressure at which water enters the membrane is generally referred to as liquid entry pressure, liquid breakthrough pressure, or water breakthrough pressure (in the case of aqueous solutions).

Figure 7B:
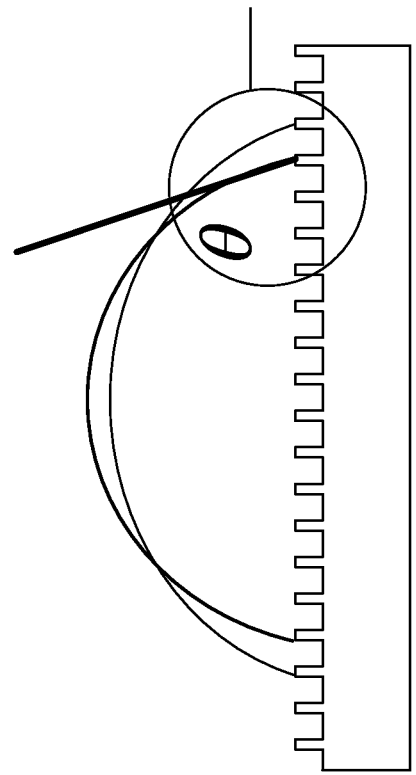
FIGS. 7A and 7B are diagrams illustrating respective contact angles for a liquid contacting different flat and textured surfaces.
Figure 7A:
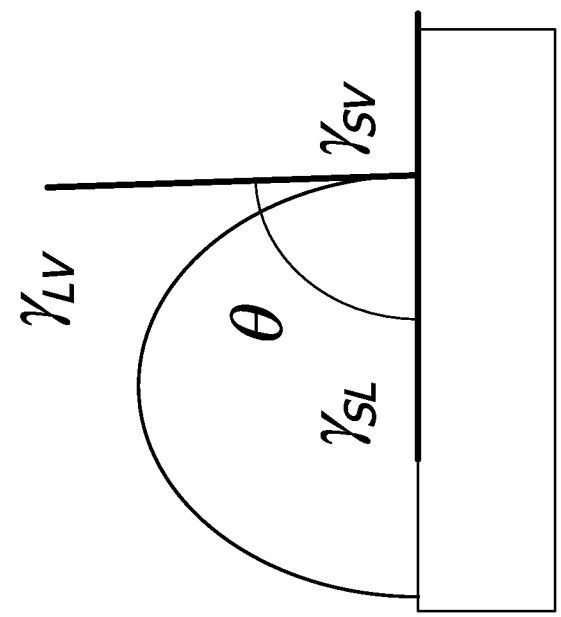

FIGS. 7A and 7B illustrate Young's equation and its relevance to the characterization of a medium as hydrophobic or hydrophilic. Surface tension $\gamma LV$ relates to the existence of an interface between a liquid and a vapor and is only one example of an interfacial tension. When a droplet of liquid rests on a solid, two further interfaces, the solid-liquid and solid-vapor, become relevant and also provide interfacial tensions $\gamma SL$ and $\gamma SV$. The balance between these three interfacial forces determines whether a droplet resting on a solid will eventually be pulled out into a film, or whether it will remain as a droplet and, if so, the extent of its footprint on the solid surface. On a smooth and flat surface, the interaction energy per unit area for a dry surface is $\gamma SV$; however, for the same surface coated in a thin layer of a liquid, there are two interfaces with a combined interaction energy per unit area of $\gamma SL+\gamma SV$. The condition for film formation on a smooth and flat surface is therefore that the energy is lowered per the following equation (1):

$$S=\gamma_{SL}+\gamma_{LV}-\gamma_{SV}>0$$

where S has been defined as the spreading power.

When a film is not formed and a droplet remains on a surface in a partial wetting state, there is an equilibrium contact angle, θe, at the edge of the droplet. This is the tangent angle of the liquid-vapor interface at the three-phase (solid-liquid-vapor) contact line. The contact angle is independent of droplet size and is described by the Young equation (2):

$$\cos\theta_e = \frac{(\gamma_{SV} - \gamma_{SL})}{\gamma_{LV}}$$

With further regard to hydrophobicity, hydrophilicity and superhydrophobicity, a completely hydrophilic (or wetting) surface is one on which a film forms so that Eq. (1) is valid and for S=0, Eq. (2) shows the threshold for this corresponds to θe=0°. A completely hydrophobic surface would be one for which it was energetically unfavorable for a droplet to have any contact whatsoever and this corresponds to θe=180°. All droplets that have finite contact angles between these two values are therefore partially wetting. Generally, if the water contact angle is smaller than 90°, the solid surface is considered hydrophilic and if the water contact angle is larger than 90°, the solid surface is considered hydrophobic. Surfaces/materials with water contact angles greater than 150° are generally called superhydrophobic.

Surfaces with hydrophobic tendencies can be enhanced to superhydrophobicity by the addition of roughness or, more accurately, a certain type of topography. This can be viewed as a physical amplification of the chemistry of the surface. It can increase the contact angle well beyond that possible by chemistry alone and can approach 180° in some cases. It can also decrease the contact angle towards 0° more than might be expected from the chemistry alone. The amplification effects of surface topography can be understood in the same manner as in deriving the Young equation. The shape of the topography and how many scales that it is rough over as well as the geometrical roughness and the contact angle of the chosen liquid on the chosen material all affect wetting and dewetting. Wenzel's equation predicts that contact angles below 90° can be decreased by roughness and higher angles are increased, but the effect of bridging allows some surfaces with lower intrinsic contact angles to show increases in contact angle with roughness. The shape of the roughness is important to induce bridging. These factors allow extensive scope when designing a material for a particular purpose such as the -phobic porous medium 208 and the optional -philic porous medium 214 employed by the capillary-based pressure threshold sensor 200.

The present disclosure exploits the fluid breakthrough pressure property of a -phobic porous medium 208 to allow some fluid 204 leaking through the medium to be detected on the other side 212 of the porous medium, which allows detection of when the pressure in a fluid line 202 rises above a pre-defined threshold. Unlike solutions involving the use of active sensors to continuously measure the pressure in a fluid line, a capillary-based pressure threshold sensor 200 in accordance with illustrative embodiments described herein is very compact and allows for very small footprint for easy integration in small devices, needs very little data processing and computing power, has no moving parts, has very low dead volume, is cost-effective, can be manufactured with minimum assembly steps, has a very low power consumption, can be mass-produced, and can be used to detect a specific pressure threshold without using any pressure transducer.

Figure 9:
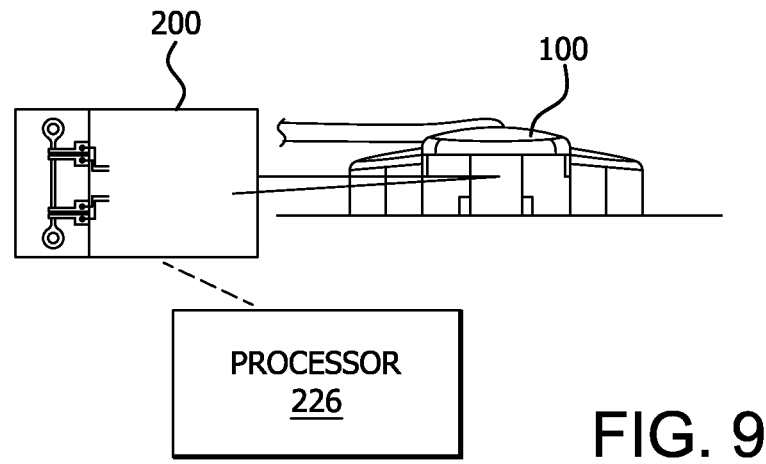
FIGS. 9, 10 and 11 illustrate, respectively, different locations for installation of a capillary-based pressure threshold sensor constructed in accordance with an illustrative embodiment in a fluid pathway of an example infusion set.
Figure 10:
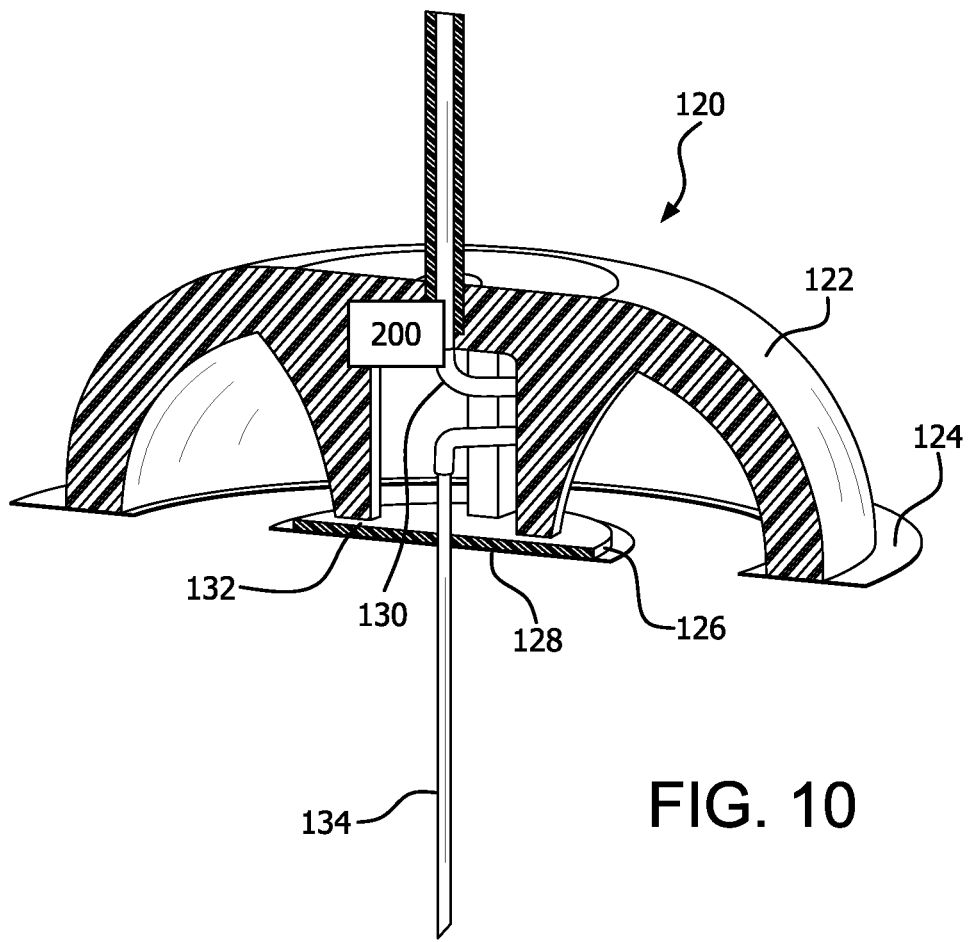
Figure 11:
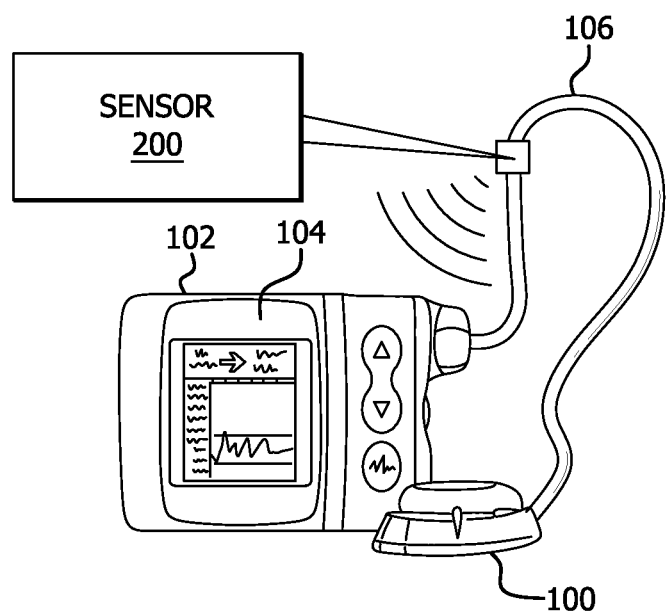

Example installations of a capillary-based pressure threshold sensor 200 in different types of devices' fluid lines 202 will now be described in accordance with illustrative embodiments. FIGS. 9, 10 and 11 illustrate, respectively, different locations for installation of a capillary-based pressure threshold sensor 200 in a fluid pathway of example infusion sets. The example infusion sets are described in commonly-owned U.S. Ser. No. 10/398,852 and U.S. Pat. No. 9,782,536, which are each incorporated herein by reference in its entirety.

FIGS. 9 and 10 depict a sensor 200 deployed in the hub of an infusion set. FIG. 11 illustrates the sensor 200 affixed (e.g., welded) onto the tubing of an infusion set. FIGS. 9 and 11 depict wireless communication between the sensor 200 and a processor 226. With regard to FIG. 10, the device 120 comprises a housing 122 and housing adhesive 124, and a needle hub 126 and needle hub adhesive 128. A flexible connection 130 is provided between the outer housing 122 and the needle hub 126 and can be configured to accommodate a sensor 200, for example. The two hubs 122 and 126 can be attached to the surface of the skin as a single device, and can be configured such that the inner hub 126 maintains the catheter 134 position relative to the tissue in which the catheter 134 has been inserted.

Figure 12:
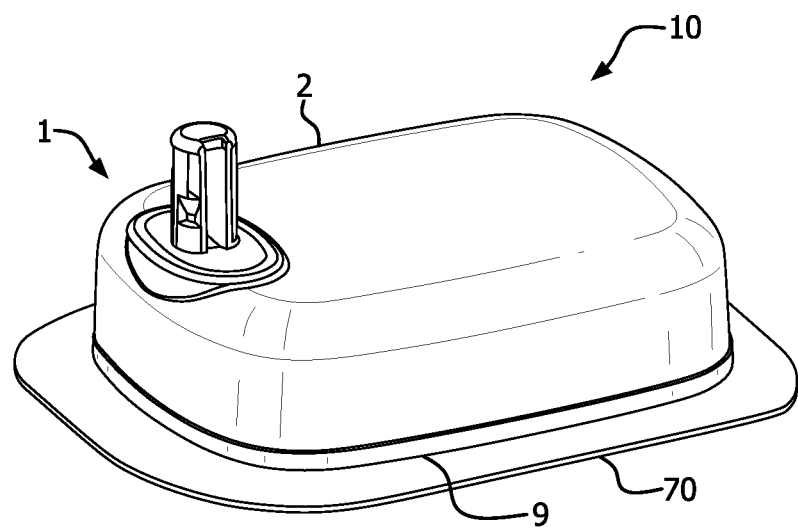
FIG. 12 is a perspective view of an example infusion pump.
Figure 13:
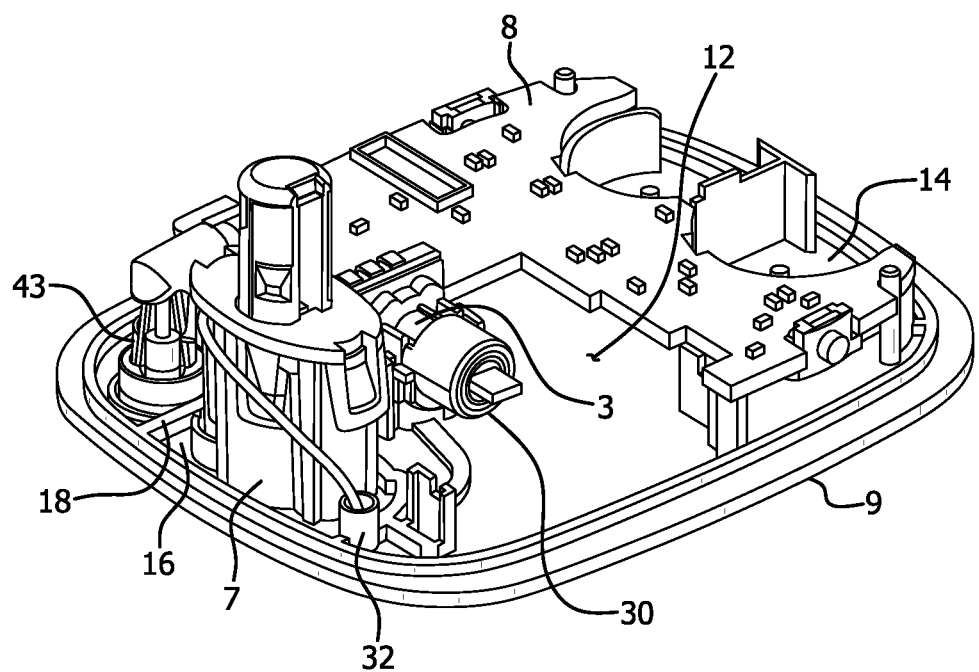
FIG. 13 is a perspective view of the infusion pump in FIG. 12 with the housing cover removed to expose example pump components on a base plate.

FIG. 12 is a perspective view of an example infusion pump in which a capillary-based pressure threshold sensor 200 can be deployed. The patch pump 1 is described in commonly-owned WO 2016048878, which is incorporated herein by reference in its entirety. The pump 1 has a housing 10, which includes a main cover 2 liquid sealed or, preferably, hermetically sealed to a base 9. The base 9 carries various components. FIG. 13 illustrates some of the main components of the patch pump 1 in a perspective view with the main cover 2 and the reservoir 4 removed for clarity. According to one embodiment, a fill port 43 is a conduit for supplying the medicament to the reservoir 4. In some embodiments, the fill port 43 can include a portion that serves as part of the flow path for medicament exiting the reservoir 4. A receptacle 32 is connected to the insertion mechanism 7 by tubing, for example, to transfer the medicament to the insertion mechanism 7 prior to injection into the skin of the patient. The patch pump 1 preferably includes a reservoir 4 for storing medicament (such as insulin), a pump 3 for pumping the medicament to exit the reservoir 4, and a force sensing resistor 30 for detecting an amount of pressure in a medicament flow path. The patch pump 1 also preferably includes electronics 8 for programming and operating the patch pump 1, and an insertion mechanism 7 for inserting a cannula 47 into a skin of the patient to deliver medicament.

Figure 14:
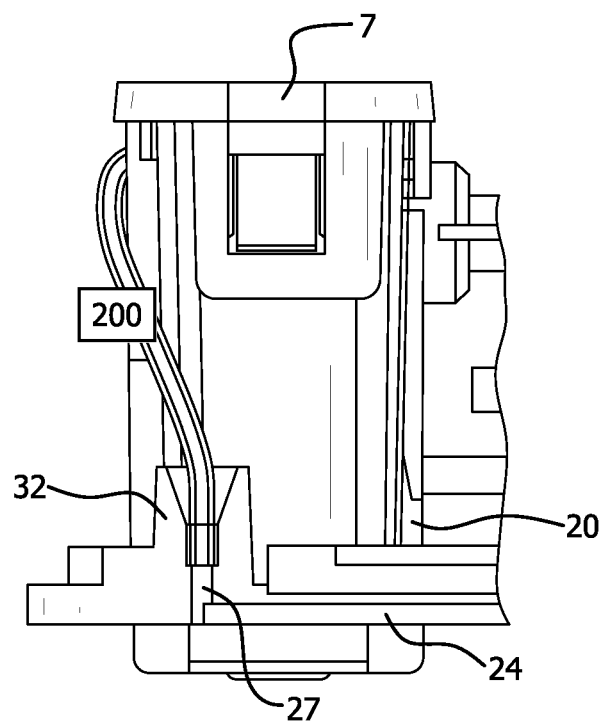
FIGS. 14, 15, 16A and 16B illustrate, respectively, different locations for installation of a capillary-based pressure threshold sensor constructed in accordance with an illustrative embodiment in a fluid pathway of an example infusion pump.
Figure 15:
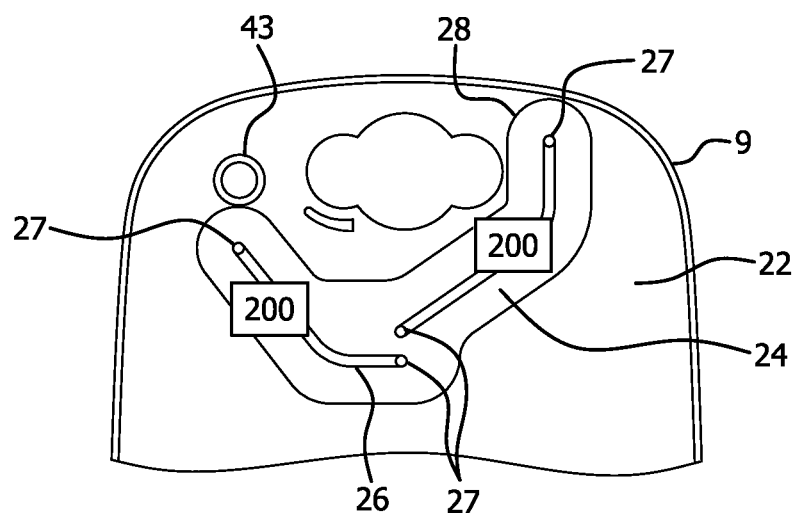

A capillary-based pressure threshold sensor 200 can be used in place of, or in addition to, an existing pressure sensor 30 in the example infusion pump 1, and the sensor 200 can be used in different locations in the fluid pathway of a fluid delivery or transport device. For example, FIG. 14 shows a capillary-based pressure threshold sensor 200 deployed along the tubing of the insertion mechanism 7. FIG. 15 illustrates a bottom surface 22 of the base 9 of the patch pump 1. The bottom surface 22 of the base 9 includes first and second fluid channels 24, 26. The first and second fluid channels 24, 26 provide fluid pathways between various components in the patch pump 1 such as the reservoir 4, the fill port 43, the force sensing resistor 30, the pump 3, and the insertion mechanism 7. A capillary-based pressure threshold sensor 200 can be deployed along one or both of the first and second fluid channels 24, 26 as shown in FIG. 15. The capillary-based pressure threshold sensor 200 can be mounted, for example, to a port in the film covering the channels. The baseplate can also have vias for connecting the sensor 200 to a processor included among the electronics 8.

Figure 16A:
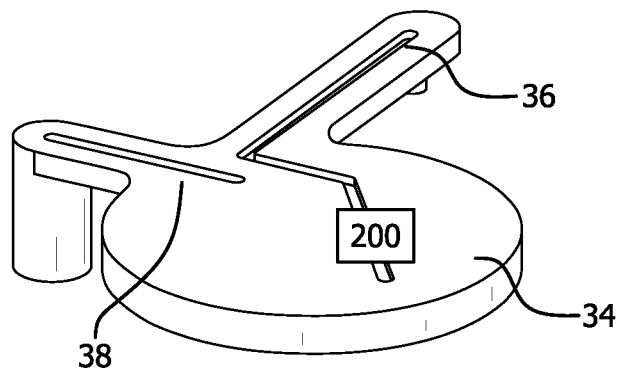
Figure 16B:
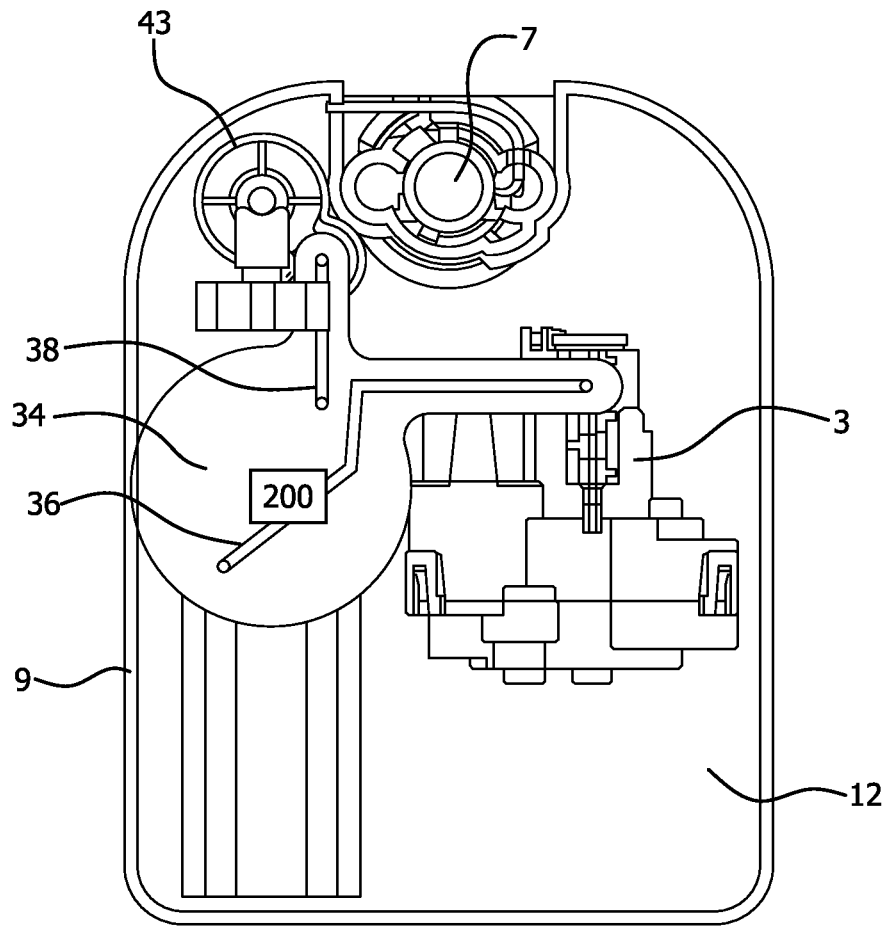

In accordance with another embodiment, a patch pump can have a flow channel plate 34 disposed in the interior 12 of the patch pump 1 to provide a medicament fluid pathway, as shown in FIGS. 16A and 16B. The flow channel plate 34 includes first and second plate fluid channels 36, 38, encapsulated by a fluid channel cover 28, which is omitted for clarity. The plate fluid channels 36, 38 route medicament fluid flow to the various components through the interior 12 of the patch pump 1. The capillary-based pressure threshold sensor 200 can be mounted, for example, to a port in the cover. The a flow channel plate 34 can also have vias for connecting the sensor 200 to a processor included among the electronics 8.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed in this document and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of claims exemplified by the illustrative embodiments by programmers skilled in the art to which the illustrative embodiments pertain. Method steps associated with the illustrative embodiments can be performed by one or more programmable processors executing a computer program, code or instructions to perform functions (e.g., by operating on input data and/or generating an output). Method steps can also be performed by, and apparatus of the illustrative embodiments can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of claims exemplified by the illustrative embodiments. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A method of making a capillary-based pressure threshold sensor comprising:
   selecting a first porous medium with a porous property that allows fluid to leak from a first side thereof, through the medium to an opposite second side thereof, the leak happening when fluid pressure exceeds the porous medium fluid breakthrough pressure threshold;
   providing a fluid detection element disposed at least proximally to the second side of the porous medium and configured to detect the presence of at least the target fluid on said second side of the porous medium; and
   configuring the first side to form a seal over a port in a fluid pathway to expose the porous medium to fluid in the fluid pathway and prevent the fluid from leaking outside the capillary-based pressure threshold sensor.

2. The method of claim 1, wherein the fluid detection element is chosen from a passive fluid detection element and an active fluid detection element,
   wherein a passive fluid detection element is not activated until the target fluid leaks through the porous medium reaching the opposite second side of the porous medium; and
   wherein an active fluid detection element provides different outputs that distinguish a first state wherein the target fluid has not yet leaked through the porous medium from a second state wherein the target fluid has leaked through the porous medium.

3. The method of claim 1, wherein the fluid detection element comprises an indicator element that is configured to change state when the target fluid has leaked through the porous medium to the second side thereof, and changing state is chosen from a color indication and a change in color indication.

4. A method of making a capillary-based pressure threshold sensor comprising:
   selecting a first porous medium with a porous property that allows fluid to leak from a first side thereof, through the medium to an opposite second side thereof, the leak happening when fluid pressure exceeds the porous medium fluid breakthrough pressure threshold;
   providing a fluid detection element disposed at least proximally to the second side of the porous medium and configured to detect the presence of at least the target fluid on said second side of the porous medium; and
   coating the first porous medium with a thermoresponsive material to detect a condition chosen from a designated temperature and a designated pressure change in the target fluid.

5. The method of claim 4, wherein the thermoresponsive material is poly-N-isopropylacrylamide (PNIPAM).

6. The method of claim 1, wherein the porous property of the medium is chosen from pore size, thickness, material, topography, coating, and contact angle with the fluid.

7. A method of making a capillary-based pressure threshold sensor comprising:
   selecting a first porous medium with a porous property that allows fluid to leak from a first side thereof, through the medium to an opposite second side thereof, the leak happening when fluid pressure exceeds the porous medium fluid breakthrough pressure threshold; and
   providing a fluid detection element disposed at least proximally to the second side of the porous medium and configured to detect the presence of at least the target fluid on said second side of the porous medium; and
   selecting a supplementary porous medium disposed at least proximally to the opposite side of the first porous medium as to be in contact with the target fluid at least before target fluid leak through the first porous medium, wherein second porous medium has one or more porous properties that allows fluid to readily infiltrate the second porous medium and achieves enhanced contact between the target fluid and the fluid detection element.

8. A method of making a capillary-based pressure threshold sensor comprising:
   selecting a first porous medium with a porous property that allows fluid to leak from a first side thereof, through the medium to an opposite second side thereof, the leak happening when fluid pressure exceeds the porous medium fluid breakthrough pressure threshold; and
   providing a fluid detection element disposed at least proximally to the second side of the porous medium and configured to detect the presence of at least the target fluid on said second side of the porous medium;
   wherein the fluid detection element comprises at least two electrodes, and further comprising:
   providing a second porous medium (-philic) disposed between the porous medium (-phobic) and the fluid detector element to controllably distribute the fluid leaking through the porous medium to the sensor, wherein the second porous medium is chosen to have different conductivity when dry and when wetted by the fluid in the fluid pathway; and
   providing the two electrodes in contact with the second side of the porous medium, the electrodes configured to be passive and not activated until fluid leaking through the porous medium exceeds the threshold.

9. The method of claim 8, wherein providing a fluid detection element comprises providing electrodes made from contact pads on a printed circuit board (PCB).

10. The method of claim 9, further comprising heat-staking the PCB via heat-staking pins configured to maintain proximity with the second porous medium and direct contact with the porous medium.

11. A method of making a capillary-based pressure threshold sensor comprising:
   selecting a first porous medium with a porous property that allows fluid to leak from a first side thereof, through the medium to an opposite second side thereof, the leak happening when fluid pressure exceeds the porous medium fluid breakthrough pressure threshold; and
   providing a fluid detection element disposed at least proximally to the second side of the porous medium and configured to detect the presence of at least the target fluid on said second side of the porous medium;

wherein the fluid detection element comprises at least two electrodes, and further comprising operating the electrodes as a passive switch that is open until it closes upon contact with the fluid.

12. A method of making a capillary-based pressure threshold sensor comprising:

selecting a first porous medium with a porous property that allows fluid to leak from a first side thereof, through the medium to an opposite second side thereof, the leak happening when fluid pressure exceeds the porous medium fluid breakthrough pressure threshold; and providing a fluid detection element disposed at least proximally to the second side of the porous medium and configured to detect the presence of at least the target fluid on said second side of the porous medium; and providing a switch that comprises providing electrodes made from contact pads on a printed circuit board (PCB).

13. The method of claim 12, further comprising connecting the electrodes to a microcontroller using a connection chosen from connecting one of the electrodes to a ground pin of a microcontroller and connecting the other electrode to an input pin of the microcontroller;

connecting one of the electrodes to an output pin of a microcontroller and connecting the other electrode to an input pin of the microcontroller; and connecting one of the electrodes to a positive rail of a power supply having common ground with the microcontroller and connecting the other electrode to an input pin of the microcontroller.

14. The method of claim 13, further connecting a pullup resistor between a positive rail of a power supply or reference voltage for the microcontroller and said input pin, said resistor having a resistance on the order of 1 k Ohm to 100 M Ohm.

15. The method of either claim 13, further connecting a pulldown resistor between said input pin and a negative rail connected to the negative or ground terminal of the microcontroller, said resistor having a resistance on the order of 1 k Ohm to 100 M Ohm.

16. A method of making a capillary-based pressure threshold sensor comprising:

selecting a first porous medium with a porous property that allows fluid to leak from a first side thereof, through the medium to an opposite second side thereof, the leak happening when fluid pressure exceeds the porous medium fluid breakthrough pressure threshold; and providing a fluid detection element disposed at least proximally to the second side of the porous medium and configured to detect the presence of at least the target fluid on said second side of the porous medium;

wherein the porous medium is chosen from a hydrophobic medium, a superhydrophobic medium, an oleophobic medium, and an amphiphobic porous medium.

17. A method of making a capillary-based pressure threshold sensor comprising:

selecting a first porous medium with a porous property that allows fluid to leak from a first side thereof, through the medium to an opposite second side thereof, the leak happening when fluid pressure exceeds the porous medium fluid breakthrough pressure threshold; and providing a fluid detection element disposed at least proximally to the second side of the porous medium and configured to detect the presence of at least the target fluid on said second side of the porous medium; and selecting a second porous medium disposed at least proximally to the first side of the first porous medium as to be in contact with the target fluid at least before target fluid leak through the first porous medium, wherein second porous medium has a porous property that:

allows fluid to readily infiltrate said second porous medium; and has a porous property that will prevent gas to pass through the second porous medium after it is infiltrated with said target fluid until gas exceeds said second porous medium gas entry pressure.

* * * * *